(12) United States Patent  
Robinson et al.

(10) Patent No.: US 11,787,918 B2  
(45) Date of Patent: Oct. 17, 2023

(54) BIOBASED COMPOSITIONS

(71) Applicant: EVOCO LIMITED, Toronto (CA)

(72) Inventors: Jason James Robinson, Toronto (CA); Radu Lucian Vicol, Toronto (CA); Juri Helmut Moebus, North York (CA); Tristan Calayan, Mississauga (CA); Guerino G. Sacripante, Oakville (CA)

(73) Assignee: Evoco Limited, Toronto (CA)

( * ) Notice: Subject to any disclaimer, the term of this patent is extended or adjusted under 35 U.S.C. 154(b) by 99 days.

(21) Appl. No.: 17/346,776

(22) Filed: Jun. 14, 2021

(65) Prior Publication Data

US 2022/0259402 A1 Aug. 18, 2022

Related U.S. Application Data

(63) Continuation of application No. 17/176,874, filed on Feb. 16, 2021, now Pat. No. 11,072,694.

(51) Int. Cl.
| | |
|---|---|
| *C08K 5/11* | (2006.01) |
| *C08G 18/42* | (2006.01) |
| *C07C 69/40* | (2006.01) |
| *C07C 69/734* | (2006.01) |
| *C07C 69/50* | (2006.01) |
| *C08G 18/18* | (2006.01) |
| *C08G 63/16* | (2006.01) |
| *C08G 18/73* | (2006.01) |
| *C07C 69/708* | (2006.01) |
| *C08G 18/08* | (2006.01) |

(52) U.S. Cl.  
CPC ............... *C08K 5/11* (2013.01); *C07C 69/40* (2013.01); *C07C 69/50* (2013.01); *C07C 69/708* (2013.01); *C07C 69/734* (2013.01); *C08G 18/18* (2013.01); *C08G 18/4238* (2013.01); *C08G 18/4286* (2013.01); *C08G 18/73* (2013.01); *C08G 63/16* (2013.01); *C08G 18/14* (2013.01); *C08G 2110/0008* (2021.01)

(58) Field of Classification Search  
CPC .. C08G 18/4238; C08G 18/4286–4288; C08K 5/11  
See application file for complete search history.

(56) References Cited

U.S. PATENT DOCUMENTS

| | | | |
|---|---|---|---|
| 2015/0018471 A1* | 1/2015 | Facklam ................ | C07C 69/40 560/190 |
| 2019/0276642 A1 | 9/2019 | Miyazaki et al. | |

FOREIGN PATENT DOCUMENTS

| | | |
|---|---|---|
| CN | 109797551 A | 5/2019 |
| JP | 2003-268143 A | 9/2003 |
| JP | 2006182874 A * | 7/2006 |
| WO | 2018/197807 A1 | 11/2018 |

OTHER PUBLICATIONS

Machine Translation of JP2006-182874A. Jul. 13, 2006. (Year: 2006).*  
Written Opinion of the International Searching Authority issued in respect of PCT/CA2022/050209.

* cited by examiner

*Primary Examiner* — Stephen E Rieth

(57) ABSTRACT

A composition comprised of a component selected from the group consisting of a biobased bis-alkyl succinate and a biobased bis-alkyl sebacate, each derived, for example, from the esterification of biobased diacid such as succinic acid or sebacic acid, and a biobased alcohol and a biobased polyester.

5 Claims, 2 Drawing Sheets wherein n is 1 (succinate) or 9 (sebacate)

R as being independently and the same or different of methyl, ethyl, n-butyl, iso-butyl, 2-octyl, cardanyl, ethoxylated cardanyl, alkyl 12-stearyl; alkyl ricinoleyl

BIOBASED COMPOSITIONS

CROSS-REFERENCE TO RELATED APPLICATION

This application is a continuation of U.S. patent application Ser. No. 17/176,874 filed on Feb. 16, 2021, the content of which is incorporated herein by reference in its entirety.

FIELD OF THE INVENTION

This disclosure is generally directed to compositions comprised of a biobased polyester, and a component selected from the group consisting of a biobased bis-alkyl succinate, a biobased bis-alkyl sebacate, and mixtures thereof; plasticizers comprised of biobased bis-alkyl succinates and biobased bis-alkyl sebacates derived, for example, from the esterification of a biobased diacid, such as succinic acid or sebacic acid, and a biobased alcohol.

OTHER RELATED APPLICATIONS

In U.S. Pat. No. 10,934,384 issued Mar. 2, 2021, there are illustrated polyurethane elastomers, foam compositions, and processes thereof, the disclosure of this patent being totally incorporated herein by reference.

In copending U.S. patent application Ser. No. 17/107,381, there are illustrated a number of biocides containing polyurethane elastomers, foam compositions, and processes thereof, the disclosure of this copending application being totally incorporated herein by reference.

In U.S. Pat. No. 10,934,385 issued Mar. 2, 2021, there are illustrated biocide containing polyurethane elastomers, foam compositions, and processes thereof, the disclosure of this patent being totally incorporated herein by reference.

BACKGROUND

A number of plasticizers can be added to polymers to, for example, render them softer, flexible, with reduced viscosity, and decreased glass transition temperatures. Examples of plasticizers utilized are phthalates, such as di-n-butyl phthalate, bis(2-ethylhexyl) phthalate, dioctyl phthalate, and the like, added to polymers such as polyvinylchloride (PVC), polyesters, polycarbonates, polystyrenes, polyethylenes, polyamides, polypropylenes and synthetic rubbers. The plastic materials of polymers and plasticizers are utilized in a wide range of applications in packaging, automotive, furniture, construction materials, aerospace, clothing, apparels, and other consumer goods. These plasticizers are synthetic chemicals derived from fossil fuels, and their production contributes heavily to greenhouse gas emission and climate change. Furthermore, phthalate plasticizers are not chemically bound to the polymers, and when used as consumer products leach out and are exposed through direct contact or indirectly through the environment, and through ingestion, inhalation, or dermal exposure have posed many adverse toxic health effects in humans. Thus, there is a need for non-toxic plasticizers, and there is also a need for plasticizers derived primarily from a biomass such that there is less dependency on fossil fuels which accelerates climate change.

Disclosed in U.S. Pat. No. 10,633,522 are renewable resin compositions that include cassava starch, polybutylene, polybutylene adipate-co-terephthalate and a non-biobased plasticizer that includes phthalate esters, and related esters, glycerol triacetate, glycerol mono and diacetates, glycerol mono, di, and tripropionates, butanoates, stearates, and acid esters such as lactic acid esters, citric acid esters, adipic acid esters, stearic acid esters, and oleic acid esters.

Illustrated in U.S. Pat. No. 10,519,296 are polyester plasticizer compositions useful as adhesives, caulk, sealants, vinyl and polymeric compositions comprising low molecular weight oligomeric dibenzoates prepared by end-capping a polyester plasticizer, having alternating units of glycols or diols and dibasic acids, with benzoic acid.

In U.S. Pat. Nos. 9,289,012 and 8,973,588, there is disclosed a plasticizer composition that can be utilized for degradable polyester filters. A filter material adapted for use as a filter element of a smoking article is disclosed, the filter material being in the form of a fibrous tow that includes a plurality of filaments of a degradable polyester and a plasticizer composition applied thereto, the plasticizer composition and the degradable polyester having a Relative Energy Difference calculated using Hansen Solubility Parameters of less than about 1.3 degradable polyester examples include polyglycolic acid, polylactic acid, polyhydroxyalkanoates, polycaprolactone, polybutylene succinate adipate, and copolymers or blends thereof. Exemplary plasticizer compositions disclosed include one or more of dimethylisosorbide, propylene carbonate, methylbenzyl alcohol, glycerol carbonate acetate, glycerol carbonate ethyl ether, and mixtures thereof, optionally in combination with triacetin.

Illustrated in U.S. Pat. No. 9,359,487 are plasticizers based on mixed esters of succinate for use in a thermoplastic polymer. The plasticizers according to the disclosure of this patent are a succinate mixed ester of benzyl on the one part and branched nonyl or decyl on the other part.

Disclosed in U.S. Pat. No. 9,550,882 are formulations for the preparation of a wiping blade element for a vehicle windscreen wiper blade. The formulation has an elastomer material based on chloroprene rubber in which plasticizing additives are incorporated, where the plasticizing additives include octyl sebacate and naphthalic oil plasticizers. Similar plasticizers are also disclosed in U.S. Pat. Nos. 6,770,372 and 6,271,294 for polymer compositions based on vinylidene fluoride resins which are particularly suitable for the manufacture of pipes, and wherein the plasticizer includes non-biobased dibutyl sebacate and non-biobased di-octyl-sebacate.

Additionally, illustrated in U.S. Pat. No. 4,085,080 are composition comprising a nylon resin, an additive insoluble in nylon and a relatively non-polar ester plasticizer selected from the group consisting of non-biobased adipate or a sebacate such as dibutyl sebacate, dihexyl sebacate, dicyclohexyl sebacate, dioctyl sebacate, didodecanyl sebacate, diphenyl sebacate and diphenyl adipate.

Moreover, disclosed in U.S. Pat. No. 4,666,968 are ester plasticizers for polyurethane compositions comprising the reaction product of an isocyanate compound and a polyol in the presence of a plasticizer compound having a solubility parameter of between about 8.3 and about 8.9 or between about 9.1 and about 9.7, and wherein the plasticizers include ditridecyl adipate, diundecyl phthalate, diisodecyl phthalate, or dibutyl phthalate.

Certain polyurethane flexible foams (PU) are known for their uses as footwear, automotive applications, yoga mats, mattresses, and the like. However, conventional petrochemical based materials being used to manufacture polyurethane (PU) flexible foams usually have a negative impact on the environment. Thus, the increase in environmental consciousness has necessitated a demand for "greener" materials that could be partially addressed by using renewable materials in the production of PU foams. Therefore, an important need resides in providing polyurethane elastomer foams with a bio-content of, for example, from about 70 percent to about 85 percent. While increasing renewable content, it is also desired to maintain or improve the performance properties of the foam. Often, when introducing biobased materials into foam formulations, there is a reduction in mechanical properties as these materials disrupt the foam network responsible for the mechanical strength. For example, in the footwear industry, mechanical strength properties, such as tensile strength, ultimate elongation, tear strength, and resilience, can be important to a foam's performance. Furthermore, excessive use of plasticizers in polymers can lead to long term leaching or separation of the plasticizer from the polymer resulting in reduction of mechanical performance and unwanted plasticizer separation from the polymer.

Polyurethane elastomers can be derived primarily from a two-component reaction or curing of a diisocyanate component and a polyol. In ideal circumstances, both the diisocyanate and polyol are in liquid form during the reaction at a temperature from about 25° C. to about 80° C. Polyols derived from ethylene oxide and or propylene oxide are typically liquid and of low viscosity under these conditions. However, these polyols are derived from fossil fuels. Polyols comprised of polyester resins with hydroxyl terminated end groups may also be used for preparing polyurethane foams, which in some instances are derived from biomass or biobased materials such as disclosed in copending application Ser. No. 17/015,669. These polyester polyols can be solid or viscous liquids at the temperature range of from about 25° C. to about 80° C., and thus require the use of diluents to render them to liquid states, and similarly with some solid diisocyanates as well. Since there is a desire to utilize biobased polyester polyols, and biobased plasticizers can be utilized as effective diluents to solubilize the polyester polyol to a liquid of low viscosity state and for providing the plasticization of the resulting polyurethane elastomer. Ideally, the amount of plasticizer should be added in a minimal enough quantity to solubilize the polyester polyol, and to provide with plasticization of the resulting polyurethane elastomer. If too much plasticizer is utilized, this can result in over plasticization with undesired mechanical performance and leaching of the plasticizer from the polyurethane. To optimally add just enough plasticizer to the formulation to achieve both solubility and plasticization properties, it is necessary to closely match the solubility parameter of the plasticizer with that of the polyester polyol and resulting polyurethane elastomer, such that the energy difference between the solubility parameters of these components is equal to or less than about 3 $Mpa^{1/2}$.

Footwear, like athletic shoes, whether for running or engaging in sports activities, lose massive amounts of energy due to impact and shock, especially in the midsoles. A well cushioned shoe disperses the impact and shock that, for a period, keeps the feet comfortable and prevents the feet from hurting. High performance athletic shoes have well cushioned midsoles that transfers the impact into forward motion or lift-off spring-like effect, as if the impact/shock is being turned into a return energy.

There is a need for polyurethane elastomers that can be selected for molded flexible parts, footwear insoles or midsoles, and which elastomers with, for example, a combination of specific mechanical properties, such as a hardness of, for example, from about 20 to about 60 Asker C, from about 15 to about 60 Askar C, from about 20 to about 50 Asker C, and from about 15 to about 35 Askar C, and for insoles a hardness of, for example, from about 22 Asker C to about 44 Asker C, and for midsoles a hardness of from about 40 to about 60 Asker C, and wherein said polyurethane elastomer composition is derived from a biobased polyester, a biobased plasticizer and a diisocyanate, and other additives such as dyes, surfactants, crosslinkers, chain extenders and diisocyanates, and wherein the polyurethane has a high biomass content of over 75 percent by weight, and wherein the solubility parameter of the plasticizer, the polyester polyol and resulting polyurethane elastomer have an energy difference between the solubility parameters of these components of less than about 3 $Mpa^{1/2}$.

Also, there is a need for compositions and processes for flexible polyurethane elastomer foams with improved characteristics, and that includes as a component a biobased polyol polyester, which are hydrolytically stable, and comprised of biobased polyester polyols with a solubility parameter of from about 8 to about 10 $Mpa^{1/2}$, and a component of a biobased plasticizer with a solubility parameter of, for example, from about 8 to about 10 $Mpa^{1/2}$, and wherein the difference in solubility parameter between the polyester polyol and the biobased plasticizer is less than 5 $Mpa^{1/2}$, less than 3 $Mpa^{1/2}$, or less than 1.3 $Mpa^{1/2}$, such that optimal compatibility is achieved. When the difference in solubility parameter between the polyester polyol and plasticizer is less than 5 $Mpa^{1/2}$, in solubility parameter between the polyester polyol and plasticizer is less than 5 $Mpa^{1/2}$, the resulting polyurethane elastomer with the other additives and diisocyanates results with minimal required plasticizer and better overall mechanical performance.

Another need is the hydrolytic stability of a polyurethane elastomer. Hydrolysis can be described as the reaction between water and a polymeric material in which a definite chemical change occurs. Materials which do not react with water can be said to possess 100 percent hydrolytic stability. Polyurethanes can be hydrolyzed by water under certain conditions and the chemical changes involved result in a deterioration in properties of the material. These changes can be followed chemically or physically but under severe conditions the degradation is readily apparent. In this case, the polyurethane can change from being a tough elastic material to a soft plastic substance with little or no strength. There is a need for compositions and processes for flexible polyurethane elastomer foams to have hydrolytic stability in which the ratio of mechanical properties after hydrolysis divided by that before hydrolysis should be above about 80 percent for both tensile strength and percent elongation.

There is also a need for polyurethane compositions for athletic shoes to receive and release high energy upon impact on striking a surface, thereby having superior energy return, in addition to a resilience which is the ability to spring back into its original shape (elasticity) after being compressed (measured by the rebound percentage). Athletic shoes lose massive amounts of energy due to shock impact, especially in areas around the midsole. A well cushioned shoe helps disperse this shock impact energy effectively thereby keeping the feet comfortable and preventing them from hurting. The disclosed polyurethane foam-based midsoles have a number of desired characteristics, such as for example, a return energy of from about 50 percent to about 100 percent, from about 55 to about 75 percent, and from about 55 to about 65 percent as measured by VF Corporation with their proprietary equipment, hydrolytic stability, excellent resilience of, for example, from about 25 percent to about 60 percent, from about 30 percent to about 60 percent, from about 25 percent to about 45 percent, and improved compression sets.

Further, there is a need for polyurethane elastomers selected for insoles and midsoles with excellent mechanical properties, and where the insoles have in embodiments a density (gram/centimeters$^3$) of, for example, from about 0.2 to about 0.3; a hardness (Asker C) of, for example, from about 15 to about 45; an elongation of from about 450 percent to about 650 percent; a tensile strength of equal to or greater than about 20 MPa; a tear strength of equal to or greater than about 2 Newtons/millimeters; a rebound test resilience of from about 40 to about 55 percent; a compression set of equal to or less than about 6 percent; and a hydrolytic stability of equal to or at least 80 percent; and for midsoles, a density in gram/centimeter$^3$ of less than about 0.5; a hardness (Asker C) of from about 30 to about 50; an elongation of greater than about 300 percent; a tensile strength in MPa of greater than about 10; a tear strength in Newtons/millimeters$^2$ of greater than about 3; a rebound test resilience of greater than about 60; a compression set of less than about 20 percent; an abrasion of less than about 300 percent; and a hydrolytic stability of at least 80 percent, and that are clear in color or white in color.

There is a need for athletic shoes with superior energy return, that is the ability of footwear, such as athletic shoes, to receive and release energy upon impact on striking the ground versus resilience, which is the ability to spring back into its original shape (elasticity) after being compressed and measured by the rebound percentage. Athletic shoes, whether for running or engaging in sports activities, lose massive amounts of energy due to impact and shock, especially in the midsoles. A well cushioned shoe disperses the impact and shock that keeps the feet comfortable and prevents the feet from hurting. High performance athletic shoes have well cushioned midsoles that transfer the impact into forward motion or lift-offspring-like effect, as if the impact/shock is being turned into a return energy. The disclosed polyurethane foam-based midsoles have a number of desired characteristics, such as for example, a return energy of from about 50 percent to about 100 percent, from about 55 to about 75 percent, and from about 55 to about 65 percent as measured by VF Corporation with their proprietary equipment, hydrolytic stability, excellent resilience of, for example, from about 25 percent to about 60 percent, from about 30 percent to about 60 percent, from about 25 percent to about 45 percent, and improved compression sets.

These and other needs can be achievable with the biobased plasticizers containing compositions polyurethane elastomers of the present disclosure.

SUMMARY

In embodiments of the present disclosure, there is disclosed a plasticizer for use in a variety of polymers to reduce its viscosity, increase flexibility and/or reduce the glass transition temperature of the polymer, and wherein the plasticizer is comprised of a biobased dialkyl succinate or a biobased dialkyl sebacate, and wherein the plasticizers are derived from a biobased or biomass derived organic acid such as succinic acid, sebacic acid, dimer diacid, dodecanedioic acid, and a biomass or biobased derived organic alcohol such as methanol, ethanol, propanol, n-butanol, iso-butanol, 2-octanol, cardanol, ethoxylated cardanol, alkyl 12-hydroxy stearate and alkyl ricinolate.

There is provided in embodiments of the present disclosure biomass or biobased plasticizers comprised of di-methyl succinate, di-ethyl succinate or bis(ethyl) succinate, bis(n-butyl) succinate, bis(propyl) succinate, bis(2-butyl) succinate, bis(2-octyl) succinate, bis(cardanol) succinate, bis(ethoxy-cardanolyl) succinate, bis(12-alkyl stearyl) succinate, di-methyl sebacate, di-ethyl sebacate or bis(ethyl) sebacate, bis(n-butyl) sebacate, bis(propyl) sebacate, bis(2-butyl) sebacate, bis(2-octyl) sebacate, bis(cardanol) sebacate, bis(ethoxy-cardanolyl) sebacate, bis(12-alkyl stearylol) succinate, bis(12-alkyl stearylol) sebacate, bis(12-alkyl ricinoleyl) succinate, bis(12-alkyl ricinoleyl) sebacate, mixtures thereof, and the like.

Yet additionally, there are disclosed plasticizers comprised of bis-alkyl succinate and bis-alkyl sebacate derived from the esterification of biobased diacids, such as succinic acid or sebacic acid, with a biobased alcohol, such as methanol, ethanol, propanol, n-butanol, iso-butanol, 2-octanol, cardanol, ethoxylated cardanol, alkyl 12-hydroxy stearate and alkyl ricinolate, which can be especially selected for polyurethanes, such as polyurethane flexible foams (PU), for their applications as footwear, automotive parts, yoga mats, mattresses, and the like.

Further, there is disclosed a biomass derived from or biobased polyester polyols derived from a biobased diol, a biobased diacid and optionally a biobased organic acid-alcohol and polymers thereof, such as polyurethane elastomers, derived from a di-isocyanate, a biobased polyester polyol and comprising biobased plasticizers, and wherein the bio-content of the polyurethane elastomer is from about 70 to about 99 percent by weight.

Additionally, there is provided in embodiments of the present disclosure, biomass or biobased plasticizers, and wherein the estimated difference in solubility parameter between the plasticizer and polymer is equal to or less than about 3 Mpa$^{1/2}$, the solubility parameter being described in Hansen Solubility Parameters: A User's Handbook, Second Edition, CRC press, 2007 (ISBN9780429127526), the disclosure of which is totally incorporated herein by reference.

Illustrated herein is also a biobased plasticizer comprised of a component selected from the group consisting of biobased bis-alkyl succinate, bis-alkyl sebacate, and mixtures thereof, with specific examples of biobased plasticizers being di-methyl succinate, diethyl succinate, bis(ethyl) succinate, bis(n-butyl) succinate, bis(propyl) succinate, bis(2-butyl) succinate, bis(2-octyl) succinate, bis(cardanol) succinate, bis(ethoxy-cardanolyl) succinate, bis(12-alkyl stearyl) succinate, di-methyl sebacate, di-ethyl sebacate or bis(ethyl) sebacate, bis(n-butyl) sebacate, bis(propyl) sebacate, bis(2-butyl) sebacate, bis(2-octyl) sebacate, bis(cardanol) sebacate, bis(ethoxy-cardanolyl) sebacate, bis(12-alkyl stearylol) succinate, bis(12-alkyl stearylol) sebacate, bis(12-alkyl ricinoloyl) succinate, bis(12-alkyl ricinoloyl) sebacate, and mixtures thereof.

Also, disclosed is a composition comprised of a polymer and a plasticizer comprised of a component selected from the group consisting of biobased bis-alkyl succinate and biobased bis-alkyl sebacate.

Further, there are disclosed polyurethane elastomers comprised of a plasticizer comprised of a component selected from the group consisting of biobased bis-alkyl succinate and bis-alkyl sebacate, and a) an organic diisocyanate, (b) a polyester resin, (c) a chain extender, (d) a crosslinker, (e) a surfactant, (f) an optional foaming agent, (g) an optional colorant, and a (h) a catalyst, wherein the polyester can be generated from the reaction of an organic diacid and an organic diol; wherein the foaming agent is present, the colorant is present and is comprised of a dye or a pigment, and wherein said organic diisocyanate is selected from the group consisting of diphenylmethane 4,4'-diisocyanate, isophorone diisocyanate, dicyclohexylmethane 4,4-diisocyanate, hexamethylene 1,6-diisocyanate, naphthalene 1,5-diisocyanate, and mixtures thereof.

Additionally, disclosed are biobased plasticizers comprised of bis-alkyl succinate and bis-alkyl sebacate derived from the esterification of biobased diacid such as succinic acid or sebacic acid, and a biobased alcohol such as ethanol, propanol, n-butanol, iso-butanol, 2-octanol, cardanol, ethoxylated cardanol, alkyl 12-hydroxy stearate and alkyl ricinolate, which plasticizers can be selected for the incorporation into polyesters, polyols, polycarbonates, polyvinylchloride, polyurethane, polystyrene, polyamide, and wherein the energy difference between the solubility parameters of the polymer and plasticizer is, for example, equal to or less than about 3 $Mpa^{1/2}$.

Also, disclosed is a polyurethane elastomer with improved characteristics that includes a biobased polyol polyester, which is hydrolytically stable, and is comprised of biobased polyester polyols with a solubility parameter of, for example, from about 8 to about 10 $Mpa^{1/2}$, and a biobased plasticizer with a solubility parameter of, for example, from about 8 to about 10 $Mpa^{1/2}$, and wherein the difference in the solubility parameter between the polyester polyol and biobased plasticizer is equal to or less than 5 $Mpa^{1/2}$, less than 3 $Mpa^{1/2}$, or less than 1 $Mpa^{1/2}$, such that optimal compatibility of these components is achieved.

Yet further disclosed herein are polyester polyols, such as a biomass or biobased derived polyester polyols derived from the polycondensation of organic diols with the number of carbon atoms being, for example, from 1 to about 18, such as 1,2-propylene glycol, 1,3-propylene glycol, 1,4-butylene glycol, dimer diols, and suitable organic diacids with the number of carbon atoms being from 1 to about 18, such as succinic acid, sebacic acid, dimer diacids, and optionally a suitable organic acid-alcohol, such as 12-hydroxy stearic acid and ricinoleic acid, copolymers, and terpolymers and the like.

Also, disclosed herein are polyurethane elastomer compositions, which in embodiments are comprised of and can be generated from the mixing and reacting of, or more specifically, obtained by mixing of and then reacting (a) an organic diisocyanate, (b) a polyester resin, (c) a chain extender comprised of a polyhydric alcohol, (d) a crosslinker, (e) a plasticizer, (f) a surfactant, (g) a foaming agent, and (h) an optional colorant, such as a dye; and wherein the elastomers and foams thereof have, for example, a hardness value of from about 15 or 20 Asker C to about 60 Asker C; a tensile strength of, for example, from about 1 MPa to about 10 MPa; a resilience of, for example, from about 25 percent to about 60 percent; and an elongation at break of, for example, from about 150 percent to about 700 percent, and a tear strength of, for example, from about 2 Newtons/millimeters to about 4 Newtons/millimeters, and wherein the polyurethane has a high biomass content of equal to or exceeding 75 percent by weight, and wherein the solubility parameter of the plasticizer, the polyester polyol and resulting polyurethane elastomer have an energy difference between the solubility parameters of these components of equal to or less than about 3 $Mpa^{1/2}$.

BRIEF DESCRIPTION OF DRAWINGS

Embodiments will now be described more fully with reference to the accompanying drawings in which.

EMBODIMENTS

Polyesters

Figure 1:
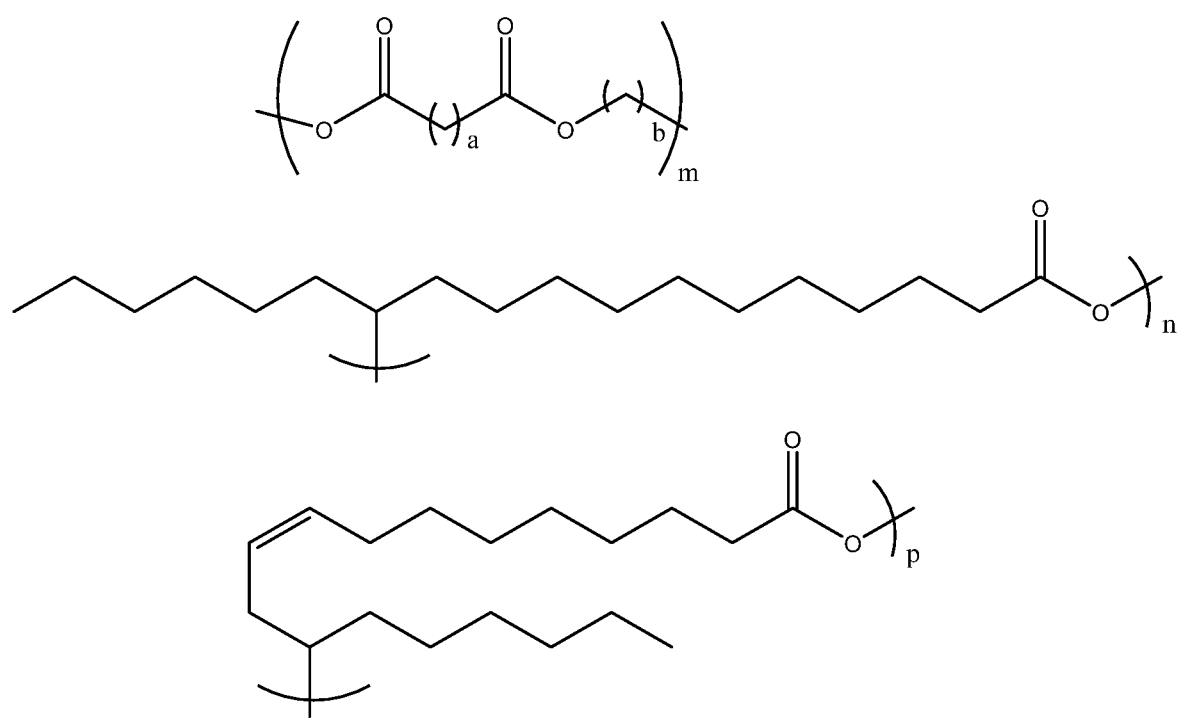
FIG. 1 is a plurality of structures of polyester resins in accordance with the subject application.

The disclosed biobased polyester polyol resins include the hydrophobic polyester resins of FIG. 1, and can be prepared by a polycondensation process by reacting suitable organic diols and suitable organic diacids, and optionally a suitable organic acid-alcohol in the presence of polycondensation catalysts. Generally, a stoichiometric equimolar ratio of organic diol and organic diacid is utilized, however, an excess of organic diol can be selected such that the resulting polymer displays a hydroxyl number of from about 30 to about 60, an acid number of equal to or less than about 5 milligrams/gram of KOH, and more specifically, less than about 3 milligrams/gram of KOH, and with a molecular weight average of from about 1,500 to about 5,000 Daltons as determined by GPC. In some instances, where the boiling point of the organic diol is from, for example, about 180° C. to about 230° C., an excess amount of diol, such as an alkylene glycol like ethylene glycol or propylene glycol of from about 0.2 to 1 mole equivalent, can be utilized and removed during the polycondensation process by distillation. The amount of catalyst utilized varies, and can be selected in amounts as disclosed herein, and more specifically, for example, from about 0.01 percent by weight to about 1 percent by weight, or from about 0.1 to about 0.75 percent by weight based on the crystalline polyester resin.

Examples of organic diacids or diesters selected for the preparation of the amorphous polyester resins and the semicrystalline polyester resins include succinic acid, fumaric acid, itaconic acid, glutaric acid, adipic acid, suberic acid, azelaic acid, sebacic acid, 1,12-dodecane dioic acid, C-18 dimer acids, such as 1,16-octadecanedioic acid, phthalic acid, isophthalic acid, terephthalic acid, naphthalene-2,6-dicarboxylic acid, naphathalene-2,7-dicarboxylic acid, cyclohexane dicarboxylic acid, malonic acid and mesaconic acid, and diesters or anhydrides thereof. The organic diacid is selected in an amount of, for example, from about 40 to about 60 percent by weight of the polyester resin. The organic diacid selected can also be those obtained through fermentation processes, natural sources like chemically derived from natural (biobased) sources, such as succinic acid, fumaric acid, itaconic acid, sebacic acid, 1,12-dodecanedioic acid, 2,5-furandicarboxylic acid, azelaic acid, dimer acids, which include aliphatic dimer acids with from about 2 carbon atoms to about 36 carbon atoms, such as C-18 dimer acids, or dimerized fatty acids of dicarboxylic acids prepared by dimerizing unsaturated fatty acids obtained from tall oil, usually on clay catalysts; hydrogenated/saturated dimer acids; and other known suitable organic acids.

The organic diol reactant selected can also be obtained from biomasses generated through fermentation processes, natural sources, and chemically derived from natural sources, and which reactant is, for example, 1,5-pentanediol, 1,2-propanediol(1,2-propylene glycol), 1,3-propanediol, 1,4-butanediol, 1,10-decanediol, 1,9-nonanediol, dimer diols, which include aliphatic dimer diols with from about 2 carbon atoms to about 36 carbon atoms, such as PRIPOL® and aliphatic diol reactant examples with, for example, from about 2 carbon atoms to about 36 carbon atoms, such as 1,2-ethanediol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,12-dodecanediol, 2-ethyl-2-butyl-1,3-propanediol, alkylene glycols like ethylene glycol, propylene glycol, monoethylene glycol, diethylene glycol, monopropylene glycol, dipropylene glycol, isosorbide, mixtures thereof, and the like. The organic diol is selected, for example, in an amount of from about 45 percent by weight to about 65 percent by weight of the polyester.

Examples of organic acid-alcohols selected for the preparation of the amorphous polyester resins and co-polyester resins as illustrated in FIG. 1 include 12-hydroxystearic acid, ricinoleic, and which is obtained from natural sources and chemically derived from natural sources, and is optionally selected, for example, in an amount of from about 5 percent by weight to about 100 percent by weight of the polyester. As will be understood, in FIG. 1, a is an integer of from about 1 to about 10, and b is an integer of from about 1 to about 18; m, n and p are the random segments of the polyester resin (or copolymer); and wherein m is the segment of the polyester resin derived from the organic diacid and organic diol, and can be an integer of from about 10 to about 1,000 random units of the polymer; n is the segment of the organic acid-alcohol (12-hydroxy stearic acid) with the copolymer containing the m segment, and can be an integer of from about 0 to about 1,000 random units of the polymer; and p is the segment of the optional organic acid-alcohol (ricinoleic acid) with the copolymer containing the m unit, and can be an integer from about 0 to about 1,000 random units of the polymer.

In embodiments of the present disclosure, examples of specific dimer diols and dimer diacids are 12-hydroxystearic acids which enables enhanced hydrophobic characteristics, and thus excellent hydrolytically stable characteristics for the polyesters include, more specifically, as dimer acids PRIPOL® 1013, PRIPOL® 1017, PRIPOL® 1009, and PRIPOL® 1012, and the dimer diols, PRIPOL® 2033, and PRIPOL® 2043.

Biobased polyesters include those resins derived from biobased organic diacids, diols and acid-alcohols, including poly(1,2-propylene-succinate), poly(1,2-propylene-sebacate), poly(1,3-propylene-succinate), poly(1,3-propylene-sebacate), poly(1,4-butylene-succinate), poly(1,4-butylene-sebacate), poly(1,2-propylene-azeleate), poly(1,2-propylene-azeleate), copoly(1,2-propylene succinate)-copoly(1,3-propylene succinate), copoly(1,2-propylene sebacate)-copoly(1,3-propylene sebacate), poly-12-hydroxy stearate, poly-riciniloate, copoly(1,2-propylene succinate)-copoly(12-hydroxy stearate), copoly(1,2-propylene-sebacate)-copoly(12-hydroxy stearate), copoly(1,3-propylene succinate)-copoly(12-hydroxy stearate), copoly(1,3-propylene sebacate)-copoly(12-hydroxy stearate), copoly(1,2-propylene succinate)-copoly(1,2-propylene sebacate), copoly (1,3-propylene succinate)-copoly(1,3-propylene sebacate), terpoly(1,2-propylene succinate)-terpoly(1,3-propylene-succinate)-terpoly(12-hydroxy stearate), copoly(1,2-propylene succinate)-copoly(riciniloate), copoly(1,2-propylene-sebacate)-copoly(riciniloate), copoly(1,3-propylene succinate)-copoly(riciniloate), copoly(1,3-propylene sebacate)-copoly(12-ricinolate), terpoly(1,2-propylene succinate)-terpoly(1,3-propylene-succinate)-terpoly(12-hydroxy stearate), terpoly(1,2-propylene succinate)-terpoly(1,3-propylene-succinate)-terpoly(riciniloate), mixture thereof and the like.

Specific biobased polyester polyols include those obtained from bio derived organic diols, such 1,2-propylene glycol, 1,3-propanediol, 1,4 butanediol, isosorbide, dimer-diols, and bio derived diacids, such as succinic acid, sebacic acid, adipic acid, furan-dioic acid, dodecanedioic acid, dimer diacid, and optionally a biobased organic acid-alcohol, such as 12-hydroxystearic acid or riciniloeic acid.

The polyester polyol and mixtures thereof can be present in the polyurethane elastomer in various effective amounts of, for example, percent by weight of from about 1 to about 99, from about 10 to about 85, from about 18 to about 75, from about 25 to about 65, from about 30 to about 55, and from about 40 to about 60 based, for example, on the polyurethane elastomer weight.

Catalysts

Examples of polycondensation catalysts primarily utilized for the preparation of semicrystalline and amorphous polyesters include tetraalkyl titanates, dialkyltin oxide such as dibutyltin oxide, tetraalkyltin such as dibutyltin dilaurate, dialkyltin oxide hydroxide such as butyltin oxide hydroxide, aluminum alkoxides, alkyl zinc, dialkyl zinc, zinc oxide, stannous oxide, zinc acetate, titanium (iv) isopropoxide (Tyzor TE), tertiary amines, such as triethylamine, dimethylcyclohexylamine, N-methylmorpholine, N,N'-dimethylpiperazine, 2-(dimethylaminoethoxy)ethanol, diazabicyclo[2.2.2]octane, DAPCO 33 LV (33 percent triethylenediamine dissolved in 67 percent dipropylene glycol), BICAT 8109 (bismuth neodecanoate), Jeffcat-Zf-54 (bis-(2-dimethylaminoethyl)ether in dipropylene glycol), KOSMOS® 75 MEG, and the like, organometallic compounds, such as titanic esters, iron compounds, tin compounds, such as tin diacetate, tin dioctoate, tin dilaurate, the dialkyl tin salts of aliphatic carboxylic acids like dibutyltin diacetate and dibutyltin dilaurate, other suitable catalysts, and the like. More specifically, catalysts utilized are comprised of organometallic compounds like titanic esters, iron compounds, tin compounds, and other suitable known catalysts. Further, the differing catalysts of copending application Ser. No. 17/015,669, the disclosure of which has been totally incorporated herein by reference, can be selected.

The catalysts can be selected in amounts of, for example, from about 0.01 to about 5 percent by weight, from about 0.1 to about 0.8 percent by weight, and from about 0.2 to about 0.6 percent by weight, and other suitable percentages based on the starting diacid or diester used to generate the polyester resins.

In embodiments of the present disclosure, the catalysts selected for the synthesis of the polyester resins, and that are used in the preparation of the polyurethane elastomer foams remain in, or are retained therein, thus purification processes may be avoided for the polyester synthesis, and products thereof, and for the polyurethane elastomer foams.

Plasticizers

The plasticizer is as disclosed herein and is comprised, for example, of biobased bis-alkyl succinates, or biobased bis-alkyl sebacate derived from the esterification of biobased diacid, such as succinic acid or sebacic acid, with a biobased alcohol such as ethanol, propanol, n-butanol, iso-butanol, 2-octanol, cardanol, ethoxylated cardanol, alkyl 12-hydroxy stearate and alkyl ricinolate, and wherein the alkyl group is from about 1 to about 12 carbon atoms such as methyl, ethyl, propyl, butyl, iso-butyl and 2-octanol.

Figure 2:
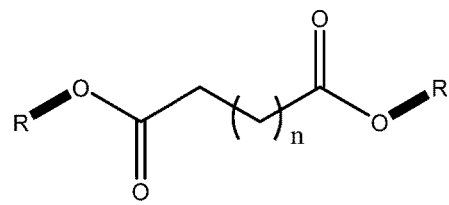
FIG. 2 is a plurality of structures of plasticizers in accordance with the subject application.
Figure 2:
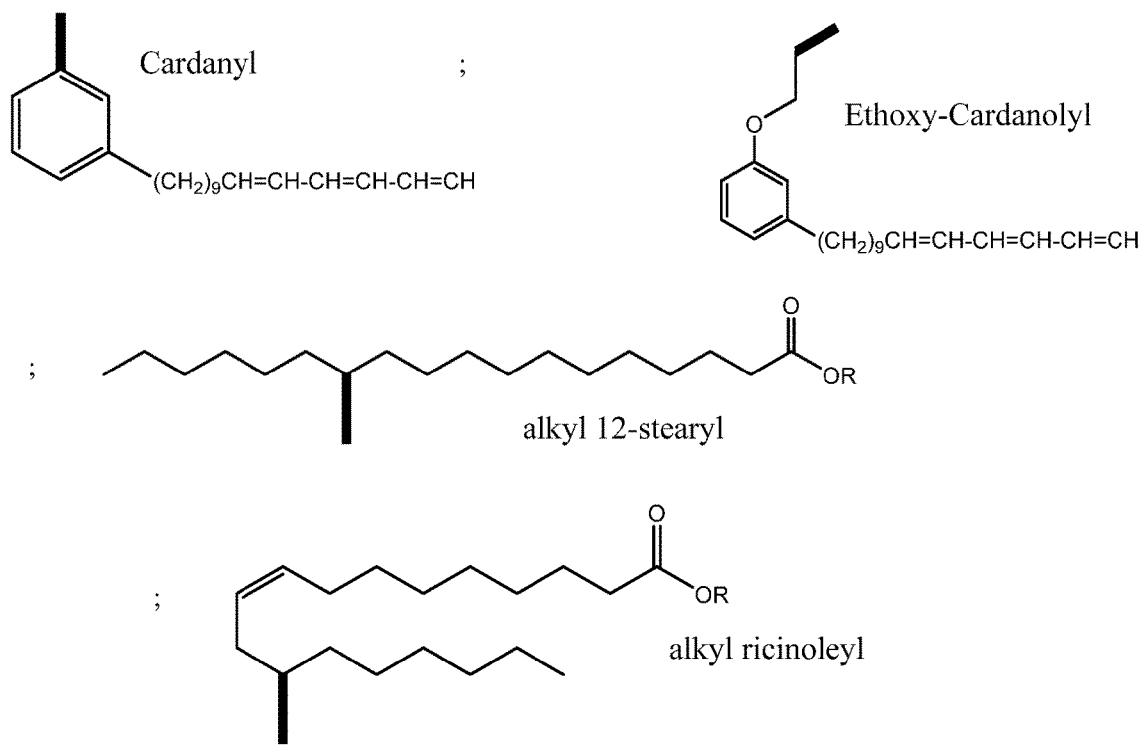

The plasticizer can be prepared, for example, from the esterification of biobased diacid such as succinic acid or sebacic acid, and a biobased alcohol such as ethanol, propanol, n-butanol, iso-butanol, 2-octanol, cardanol, ethoxylated cardanol, alkyl 12-hydroxy stearate and alkyl ricinolate. The alkyl 12-hydroxy stearate and alkyl ricinolate can be prepared from the esterification of 12-hydroxystearic acid or ricinoleic acid, and an alcohol such as methanol, ethanol, propanol, butanol, isobutanol or 2-octanol, and the like. Examples of the plasticizer are depicted in FIG. 2.

Crosslinkers

The crosslinker is, for example, selected from diethanolamine, glycerol, trimethylol propane, pentaerythritol, 1,2,4-butanetriol, thioglycolic acid, 2,6-dihydroxybenzoic acid, melamine, diglycolamine, 1,2,6-hexanetriol, glycerol, 1,1,1-trimethylolethane, 1,1,1-trimethylolpropane (TMP), triisopropanol amine, triethanol amine, tartaric acid, citric acid, malic acid, trimesic acid, trimellitic acid, trimellitic anhydride, pyromellitic acid, and pyromellitic dianhydride; trimethylolpropane, trimethylolethane; pentaerythritol, polyethertriols, tartaric acid, citric acid, malic acid, trimesic acid, trimellitic acid, trimellitic anhydride, pyromellitic acid, and pyromellitic dianhydride; trimethylolpropane, trimethylolethane; pentaerythritol, polyethertriols, and glycerol, and especially polyols, such as trimethylolpropane, pentaerythritol, and biobased materials thereof present in amounts of, for example, from about 0.1 percent by weight to about 10 percent by weight, and from about 0.1 percent by weight to about 5 percent by weight based on the amount of polyurethane elastomer, and other known suitable crosslinkers. The crosslinker in embodiments can be used to increase the molecular weight of the polyurethane by interlinking the chains thereof to provide a more rigid network.

Chain Extenders

Chain extender examples include alcohols, such as polyhydric alcohols, carboxylic acid derivatives having two functional groups can be selected for the elastomers and processes disclosed herein. More specifically, chain extender examples contain, for example, two hydroxyl moieties such as 1,2-ethanediol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,12-dodecanediol, 2-ethyl-2-butyl 1,3-propanediol; alkylene glycols like ethylene glycol, propylene glycol, monoethylene glycol, diethylene glycol, monopropylene glycol, dipropylene glycol, mixtures thereof, other known suitable chain extenders, and the like present in amounts of, for example, from about 0.1 percent by weight to about 10 percent by weight, from about 0.1 percent by weight to about 5 percent by weight based on the polyurethane elastomer, and other known suitable chain extenders. The chain extender, which can be a low molecular weight diol that reacts with a diisocyanate to provide for an increase in the block length of the polyurethane hard segment without crosslinking of the chains thereof. The increase in the block length of the polyurethane hard segment is usually proportional to the amount of chain extender used, for example, from about 0.1 percent by weight to about 10 percent by weight.

Surfactants

The surfactants that can be selected are, for example, polyether-silicone oil mix (TEGOSTAB® B4113) available from Evonik, 8383, silicone surfactant DABCO DC® 193, and TEGOSTAB® B8383 available from Evonik, sodium dodecylbenzene sulfonate, sodium dodecylnaphthalene sulfate, dialkylbenzenealkyl, sulfates and sulfonates, adipic acid, available from Aldrich, NEOGEN R™, NEOGEN SC™, available from Daiichi Kogyo Seiyaku, polyvinyl alcohol, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxypoly(ethyleneoxy) ethanol, available from Rhodia as IGEPAL CA-210™, IGEPAL CA-520™, IGEPAL CA-720™, IGEPAL CO-890™, IGEPAL CO-720™, IGEPAL CO-290™, ANTAROX 890™, and ANTAROX 897™, and other suitable known surfactants in amounts of, for example, from about 0.1 percent by weight to about 10 percent by weight, and from about 0.1 percent by weight to about 3 percent by weight based on the polyurethane elastomer amount.

Colorants

Colorant examples that can be selected for the preparation of the polyurethane elastomer compositions present, for example, in amounts of from about 1 percent by weight to about 10 percent by weight, 0.1 percent by weight to about 5 percent by weight, and from about 0.1 percent by weight to about 3 percent by weight based on the amount of the polyurethane elastomer include pigments, dyes, mixtures thereof, and the like. Examples of dyes and pigments include inorganic pigments, such as carbon black, whiteners, such as titanium oxide which has weather resistance, and organic pigments and dyes, such as phthalocyanine blue, azo dyes, Indigo, Congo Red, Methyl Orange, Malachite Green, purple dyes, brown dyes, black dyes, Pigment Blue 15:3 or C.I. Pigment Blue 15:4, phthalocyanine green, quinacridone red, indanthrene orange, and isoindolinone yellow, C.I. Pigment Red 254 and C.I. Pigment Red 122, C.I. Pigment Yellow 151 and C.I. Pigment Yellow 74, Fates Dye and Keen Dye available from BAO Shen Polyurethane Tech.LTD-China, and other suitable known colorants, such as known dyes and pigments illustrated in the Color Index (C.I.), such as known magenta, yellow, and cyan colorants.

Foaming Agents

There is selected as the foaming (or blowing) agent water and other suitable known blowing agents present in the reaction mixture and in the flexible polyurethane foams thereof, and which increases the firmness of the resulting foams. A soft, flexible, plasticized water-blown polyurethane foam composition can be produced from the reaction of a natural polyol and methylene diphenyl diisocyanate, (MDI) or an equivalent isocyanate, and by optionally adding a plasticizer.

Specific examples of foaming agents include water, compressed gases, such as $CO_2$, $N_2$, air or low boiling liquids like cyclopentane, pentane, isobutane and hydrofluorocarbons, added in amounts of from about 0.03 to about 10 percent by weight, and from about 0.5 percent by weight to about 3 percent by weight of the polyurethane elastomer. Also, for example, $CO_2$ may be generated insitu by the decomposition of $NaHCO_3$ or the reaction of water with isocyanate.

Organic Diisocyanates

Examples of organic diisocyanates selected for the compositions and processes illustrated herein include aliphatic diisocyanates, such as hexamethylene diisocyanate, cycloaliphatic diisocyanates, such as isophorone diisocyanate, cyclohexane 1,4-diisocyanate, 1-methylcyclohexane 2,4-diisocyanate, and 1-methylcyclohexane 2,6-diisocyanate, and the corresponding isomer mixtures, dicyclohexylmethane 4,4'-diisocyanate, dicyclohexylmethane 2,4'-diisocyanate, dicyclohexylmethane 2,2'-diisocyanate, and the corresponding isomer mixtures, aromatic diisocyanates, such as tolylene 2,4-diisocyanate, mixtures of tolylene 2,4-diisocyanate and tolylene 2,6-diisocyanate, diphenylmethane 4,4'-diisocyanate, diphenylmethane 2,4'-diisocyanate, and diphenylmethane 2,2'-diisocyanate, mixtures of diphenylmethane 2,4'-diisocyanate and diphenylmethane 4,4'-diisocyanate, urethane-modified liquid diphenylmethane 4,4'-diisocyanates or diphenylmethane 2,4'-diisocyanates, 4,4'-diisocyanato-1,2-diphenylethane, and naphthylene 1,5-diisocyanate. Especially selected diisocyanates are hexamethylene 1,6-diisocyanate, cyclohexane 1,4-diisocyanate, isophorone diisocyanate, dicyclohexylmethane diisocyanate, diphenylmethane diisocyanates with more than 96 percent by weight content of diphenylmethane 4,4'-diisocyanate, diphenylmethane 4,4'-diisocyanate, and naphthylene 1,5-diisocyanate, suitable known diisocyanates, and mixtures thereof, and is selected in an amount of, for example, from about 10 percent by weight to about 40 percent by weight, and from about 15 percent by weight to about 25 percent by weight based on the polyurethane elastomer amount.

In embodiments, there can be selected mixtures of a diisocyanate and a polyisocyanate in an amount of up to about 15 percent by weight, based on the total diisocyanates present, however, up to about 40 percent by weight of polyisocyanate can be added, and that provides an improved thermoplastically processable product. Examples of polyisocyanates include triisocyanates, biurets and isocyanurate trimer. For example, triphenylmethane 4,4',4"-triisocyanate and polyphenylpolymethylene polyisocyanates as well as hexamethylene diisocyanate (HDI) biuret trimer, isocyanurate trimer, and isophorone (IPDI) isocyanurate trimer.

The characteristics and properties of the polyurethane products can be measured as illustrated herein, and by known processes and devices. More specifically, there was selected as a tensile tester, the ADMET eXpert 7601 Tensile Tester, to measure tensile strength, elongation, tear strength and compression set, by preparing a sample of the polyurethane elastomer, such as a foam material in dog-bone shapes with a die cutter with a standard thickness of 10 millimeters and length of 140 millimeters based on ASTM D412, ASTM D3574-17, SATRA TM-2 standards. The sample removed was placed between clamps and where the tensile tester applies the appropriate force at a particular speed (generated by the software) on the test material sample to provide the characteristics, properties and values of the polyurethane products.

Density was measured using the equation Density=Mass/Volume, where mass represents the mass of the material in a mold measured on an analytical balance. Volume of the mold was obtained from the dimensions of the mold. For example, if a mold was producing 10 millimeters or 1 centimeter polyurethane foam plaques with dimensions length equal to 21 centimeters, width equal to 14.8 centimeters, and the thickness equal to 10 millimeters, then volume was calculated to be 21 times 14.8 times 1 equals 310.80 centimeters$^3$.

The hardness can be measured on the Asker C scale, and can also be measured by a durometer.

Bio-Content

The bio-content of the disclosed polyurethane elastomer foams can be determined by various methods. In one method, the bio-content can be measured as follows and where, for example, the biobased polyester polyol, biobased plasticizer, optionally, and biobased chain extender which also impart bio-content characteristics to the polyurethane elastomer foams.

Thus, based on the bio-content of the ingredients present in the polyurethane foam formulations, the bio-content for the polyurethane elastomer foam is, for example, from about 60 percent to about 90 percent, from about 40 percent to about 85 percent, from about 70 percent to about 85 percent, and from about 70 percent to about 80 percent.

More specifically, although it is not desired to be limited by theory, generally, for the polyurethane plasticizer foam preparation in embodiments and the appropriate Examples that follow the active reactant components of, for example, the polyester resin, the crosslinker, the chain extender, and the foaming agent, and the nonreactive components of, for example, dye, plasticizer, and surfactant are initially admixed followed by the addition of the organic diisocyanate and heating. The polyester that contains at least one hydroxyl end group, that is the polyester polyol, reacts with the diisocyanate resulting in a urethane linkage. The chain extender of, for example, 1,3-propanediol which also has hydroxyl ends reacts with the diisocyanate to generate urethane linkages. The crosslinker of, for example, diethanol amine includes two hydroxyl moieties and one amine (N—H) moiety, and where all 3 functionalities react with the diisocyanate to form either the urethane or urea linkage, respectively. Finally, the foaming agent like water reacts with the diisocyanate to result in an amine, and that amine further reacts with the diisocyanate to give the urea linkage. The elastomer foam can be referred to as a polyurethane, however, it is known and accepted that when a crosslinker like diethanolamine, and the foam agent like water are present there will be some urea linkages, albeit very small, such as less than about 3.5 percent.

TEGOSTAB® B4113 and B8383 are considered silicone surfactants; CA-210 is a surfactant of octylphenoxy poly(ethyleneoxy)ethanol; CA-520 is a polyoxyethylene (5) isooctylphenyl ether surfactant; ANTAROX® 890 is a polyoxyethylene (40) nonylphenyl ether surfactant; and ANTAROX® 897 is a poly(oxy-1,2-ethanediyl), α-(nonylphenyl)-ω-hydroxy surfactant.

Polyester polyol PSA300 is a polyester polyol with a weight average molecular weight of about 3,000; ISO is diisocyanate, a commercially available diisocyanate SUPRASEC™ 2379; MDI is diphenyl methane diisocyanate (MDI); and FATES® dye is an orange polyester dye that is commercially available. The chemical name for FATES® dye has not been disclosed by the supplier. Further, examples of dyes are timerland orange, timerland lime green, timerland dark cheddar, all available from BAO Shen Polyurethane Tech.LTD-China; and DABCO® 33LV is an amine catalyst of 33 percent TEDA (triethylene diamine) dissolved in dipropylene glycol. Abrasion refers to a material's ability to withstand wear as it encounters friction.

Specific embodiments of the present disclosure as illustrated in the following Examples are for illustrative purposes and are not limited to the materials, conditions, or process parameters set forth in these embodiments. Parts and percentages are by weight unless otherwise indicated. Also, the components can be mixed in various sequences to obtain the plasticizers, the polyurethane elastomers and the polyurethane foams, which can be biodegradable. The viscosities were measured by the Brookfield CAP2000 Viscometer. A footbed mold refers to a mold with a cavity of certain design replicating an insole or a midsole of footwear like a shoe.

The cavity has a certain volume when the formulation mixture poured and closed to form the foam product.

Example 1

Preparation of a plasticizer comprised of biobased di-n-butyl succinate.

To a 500 milliliter 3-necked flask equipped with a mechanical stirrer and a dean-stark distillation apparatus were added 100 grams of biobased succinic acid (obtained from Bio-Amber), 139 grams of biobased n-butanol (available from Butamax) and 0.1 gram of methane sulfonic acid catalyst. The resulting mixture under a nitrogen atmosphere was heated to 130° C. over a 90 minute period, where 25 grams of distillate comprised of water and n-butanol were collected in the distillation receiver. The flask was then cooled to 110° C. and an additional 50 grams of n-butanol were added. The mixture obtained was then heated to 155° C., maintained for two hours at this temperature, and more distillate was obtained. The flask was then cooled to 110° C., and another 50 grams of n-butanol were added, and the resulting mixture reheated to 155° C. for 4 more hours and until no more distillate condensed. The acid value of the product, measured using the ASTM D974 procedure, was 0.5 milligram of KOH/gram. The product, biobased di-n-butyl succinate, was then cooled to room temperature, about 25° C. throughout, and filtered through a glass filter frit (G-3 pore) equipped with 2 paper filters (medium pore) into a 250 milliliter filtration flask under slight vacuum to result in 188 grams of clear liquid. The identity of the biobased di-n-butyl succinate product was confirmed by NMR spectroscopy.

Example 2

Preparation of a plasticizer comprised of biobased bis(2-octyl) succinate.

To a 250 milliliter 3-necked flask equipped with a magnetic stirrer and a dean-stark distillation apparatus were added 50 grams of biobased succinic acid (obtained from Bio-Amber), 110 grams of biobased 2-octanol, obtained from Arkema and 0.2 gram of titanium (IV) iso-propoxide catalyst, obtained from Sigma. The resulting mixture under a nitrogen atmosphere was heated to 185° C. over a 4 hour period and maintained 185° C. until the acid value of the mixture was measured to be <1.0 milligram of KOH/gram. Nitrogen was then bubbled through the reaction mixture for an additional 30 minutes, after which the product, biobased bis(2-octyl) succinate, was cooled to room temperature and then filtered through a glass filter frit (G-3 pore) equipped with 2 paper filters (medium pore) into a 250 milliliter filtration flask under slight vacuum to result in 188 grams of clear liquid of biobased bis(2-octyl) succinate product, confirmed by NMR spectroscopy.

Example 3

Preparation of a plasticizer comprised of biobased bis (ethoxy-cardanolyl) succinate.

To a 250 milliliter 3-necked flask equipped with a magnetic stirrer and a dean-stark distillation apparatus were added 29.5 grams of biobased succinic acid (obtained from Bio-Amber), 177.4 grams of biobased ethoxylated cardanol (obtained as LITE 2020™ from Cardolite Corporation), and 0.2 gram of titanium (IV) iso-propoxide catalyst. The resulting mixture under nitrogen atmosphere was heated to 190° C. over a 4 hour period and maintained at 190° C. until the acid value of the mixture was measured to be less than about 1.0 milligram of KOH/gram. Nitrogen was then bubbled through the reaction mixture for an additional 30 minutes, after which the product, biobased bis(ethoxy-cardanolyl) succinate, was cooled to room temperature and then filtered through a glass filter frit (G-3 pore) equipped with 2 paper filters (medium pore) into a 250 milliliter filtration flask under slight vacuum to result in 196 grams of clear liquid of the biobased bis(ethoxy-cardanolyl) succinate as confirmed by NMR spectroscopy.

Example 4

Preparation of a plasticizer comprised of biobased bis(2-octyl) sebacate.

To a 250 milliliter 3-necked flask equipped with a magnetic stirrer and a dean-stark distillation apparatus were added 90.1 grams of biobased sebacic acid (obtained from Oleris Arkema), 127.5 grams of biobased 2-octanol (obtained from Oleris Arkema) and 0.2 gram of titanium (IV) iso-propoxide catalyst. The mixture under nitrogen atmosphere was heated to 185° C. over a 4 hour period and maintained at 185° C. until the acid value of the mixture was measured to be <1.0 milligram of KOH/gram. Nitrogen was then bubbled through the reaction mixture for an additional 30 minutes, after which the product, biobased bis(2-octyl) sebacate, was cooled to room temperature and then filtered through a glass filter frit (G-3 pore) equipped with 2 paper filters (medium pore) into a 250 milliliter filtration flask under slight vacuum to result in 188 grams of a clear liquid product of biobased bis(2-octyl) sebacate as confirmed by NMR spectroscopy.

Example 5

Preparation of a plasticizer comprised of biobased bis (ethoxy-cardanolyl) sebacate.

To a 250 milliliter 3-necked flask equipped with a magnetic stirrer and a dean-stark distillation apparatus were added 29.5 grams of biobased sebacic acid (obtained from Oleris Arkema), 177.4 grams of biobased ethoxylated cardanol (obtained as LITE 2020™ from Cardolite Corporation), and 0.2 gram of titanium (IV) iso-propoxide catalyst. The mixture under nitrogen atmosphere was heated to 190° C. over a 4 hour period and maintained at 190° C. until the acid value of the mixture was measured to be <1.0 milligram of KOH/gram. Nitrogen was then bubbled through the resulting reaction mixture for an additional 30 minutes, after which the product, biobased bis(ethoxy-cardanolyl) sebacate, was cooled to room temperature and then filtered through a glass filter frit (G-3 pore) equipped with 2 paper filters (medium pore) into a 250 milliliter filtration flask under slight vacuum to result in 196 grams of a clear liquid of biobased bis(ethoxy-cardanolyl) sebacate product, as confirmed by NMR spectroscopy.

Example 6

Preparation of the biobased polyester resin poly(1,3 propylene succinate) derived from 1 mole equivalent of succinic acid, and 1.1 mole equivalent of 1,3-propanediol.

To a 500 milliliter 3-necked flask equipped with a magnetic stirrer and distillation apparatus were added 130.6 grams of biobased 1,3 propanediol (available from DuPont), 184.6 grams of biobased succinic acid (available from Bioamber), and 0.1 gram of titanium (IV) isopropoxide catalyst. The obtained mixture was kept under nitrogen and heated to 190° C. for over 220 minutes with stirring at 250 rpm, and maintained at 190° C. for 7 additional hours wherein about 52 grams of water collected in the distillation receiver. The flask was then left cooling to room temperature, resulting in a viscous clear liquid product comprised of biobased poly(1,3, propylene succinate). The acid value was measured to be 0.85 milligram of KOH/g using the ASTM D974 procedure. The viscosity was measured to be 3,294 centipoise using the Brookfield CAP2000 Viscometer at 70° C.

Example 7

Preparation of the biobased polyester resin poly(1,3 propylene succinate) derived from 1 mole equivalent of succinic acid, and 1.1 mole equivalent of 1,3-propanediol.

To a 500 milliliter 3-necked flask equipped with a magnetic stirrer and distillation apparatus were added 130.6 grams of biobased 1,3-propanediol (available from Dupont), 184.6 grams of biobased succinic acid (available from Bioamber), and 0.1 gram of titanium (IV) isopropoxide catalyst. The mixture obtained was kept under nitrogen and heated to 190° C. for over 220 minutes with stirring at 250 rpm, and maintained at 190° C. for 7.5 additional hours wherein about 67.5 grams of water collected in the distillation receiver. The flask was then left cooling to room temperature resulting in a viscous clear liquid product comprised of biobased poly(1,3 propylene succinate). The acid value was measured to be 1.91 milligrams of KOH/gram using the ASTM D974 procedure. The viscosity was measured to be 4,852 centipoise using the Brookfield CAP2000 Viscometer at 70° C.

Example 8

Preparation of the biobased polyester resin copoly(1,2 propylene succinate)-copoly(1,3-propylene succinate), derived from 1 mole equivalent of succinic acid, 0.5 mole equivalent of 1,2-propylene glycol, and 0.5 mole equivalent of 1,3-propanediol.

To a 500 milliliter 3-necked flask equipped with a magnetic stirrer and distillation apparatus were added 74.5 grams of biobased 1,3-propanediol (available from Dupont), 74.5 grams of biobased 1,2-propylene glycol (available from Archer Daniels Midland), 210 grams of biobased succinic acid (available from Bioamber), and 1.0 gram of titanium (IV) isopropoxide catalyst. The mixture was heated to 180° C. over 120 minutes with stirring at 250 rpm, and maintained at 180° C. for 5 additional hours, after which an additional amount of 20 grams of 1,3-propanediol were added and maintained at 180° C. for an additional 6 hours. The flask was then left cooling to room temperature resulting in a viscous clear liquid product comprised of biobased copoly(1,2 propylene succinate)-copoly(1,3-propylene succinate). The acid value was measured to be 5.41 milligrams of KOH/gram using the ASTM D974 procedure. The viscosity was measured to be 6,693 centipoises using the Brookfield CAP2000 Viscometer at 70° C.

Example 9

Preparation of the biobased polyester resin copoly(1,3-propylene succinate), copoly(12-hydroxy-stearate) derived from 0.95 mole equivalent of succinic acid, 0.1 mole equivalent of 12-hydroxy stearic acid, and 0.96 mole equivalent of 1,3-propanediol.

To a 500 milliliter 3-necked flask equipped with a magnetic stirrer and distillation apparatus were added 136 grams of biobased 1,3-propanediol (available from DuPont), 51.6 grams of biobased 12-hydroxystearic acid (available from Archer Daniels Midland), 210 grams of biobased succinic acid (available from Blachford), and 0.4 gram of methane sulfonic acid catalyst. The mixture obtained was heated to 175° C. over 180 minutes with stirring at 250 rpm, and then heated to 200° C. over 15 minutes, and maintained at 200° C. for an additional 3 hours. About 69 grams of water were collected in the distillation receiver. The flask was then left cooling to room temperature resulting in a viscous clear liquid product comprised of biobased copoly(1,3-propylene succinate), copoly(12-hydroxy-stearate). The acid value was measured to be 1.78 milligrams of KOH/gram using the ASTM D974 procedure. The viscosity was measured to be 1,260 centipoises using the Brookfield CAP2000 Viscometer at 70° C.

Example 10

Preparation of the biobased polyester resin copoly(1,3-propylene succinate), copoly(12-hydroxy-stearate) derived from 0.925 mole equivalent of succinic acid, 0.15 mole equivalent of 12-hydroxy stearic acid, and 1.025 mole equivalent of 1,3-propanediol.

To a 500 milliliter 3-necked flask equipped with a magnetic stirrer and distillation apparatus were added 125 grams of biobased 1,3-propanediol (available from DuPont), 79 grams of biobased 12-hydroxystearic acid (available from Archer Daniels Midland), 175.9 grams of biobased succinic acid (available from Blachford), and 0.4 gram of methane sulfonic acid catalyst. The mixture was heated to 200° C. over 90 minutes with stirring at 250 rpm, and maintained at 200° C. for an additional 5 hours. About 55 grams of water were collected in the distillation receiver. The flask was then left cooling to room temperature resulting in a viscous clear liquid product comprised of biobased copoly(1,3-propylene succinate), copoly(12-hydroxy-stearate). The acid value was measured to be 1.32 milligrams of KOH/gram using the ASTM D974 procedure. The viscosity was measured to be 2,700 centipoises using the Brookfield CAP2000 Viscometer at 70° C.

Example 11

Preparation of the biobased polyester resin copoly(1,3-propylene succinate), copoly(12-hydroxy-stearate) derived from 0.875 mole equivalent of succinic acid, 0.25 mole equivalent of 12-hydroxy stearic acid, and 0.975 mole equivalent of 1,3-propanediol.

To a 500 milliliter 3-necked flask equipped with a magnetic stirrer and distillation apparatus were added 125 grams of biobased 1,3-propanediol (available from DuPont), 79 grams of biobased 12-hydroxystearic acid (available from Archer Daniels Midland), 175.9 grams of biobased succinic acid (available from Blachford), and 0.4 gram of methane sulfonic acid catalyst. The mixture resulting was heated to 185° C. over 90 minutes with stirring at 250 rpm, and then heated at 200° C. over 60 minutes, and maintained at 200° C. for an additional 4 hours. About 47 grams of water were collected in the distillation receiver. The flask was then left cooling to room temperature resulting in a viscous clear liquid product comprised of biobased copoly(1,3-propylene succinate), copoly(12-hydroxy-stearate). The acid value was measured to be 1.36 milligrams of KOH/gram using the ASTM D974 procedure. The viscosity was measured to be 2,033 centipoises using the Brookfield CAP2000 Viscometer at 70° C.

Example 12

Preparation of an insole plaque polyurethane foam derived from 60.3 weight percent of the biobased polyester resin of Example 6, 12.1 weight percent of the biobased diethyl succinate plasticizer, 22.3 weight percent of diisocyanate, 1.77 weight percent of chain extender, 2 weight percent of dye, 0.6 weight percent of catalyst, 0.33 weight percent of surfactant, 0.06 weight percent of crosslinker, and 0.53 weight percent of water.

60.3 Grams of the polyester resin of Example 6 were melted in a 400 milliliter glass can at 70° C. for 2 hours in an oven. To this was added 0.33 gram of TEGOSTAB® surfactant (available from Evonik), 1.77 grams of 1,3-propanediol (chain extender), 0.6 gram of DABCO LV® catalyst (available from Evonik), 0.53 gram of water, 0.06 gram of diethanol amine crosslinker, 2 grams of Red dye (available from BAO Shen Polyurethane Tech. LTD-China), 12.1 grams of biobased diethyl succinate, and the resulting mixture was stirred for 30 minutes at 2,000 rpm to ensure homogeneity. The mixture was then added to the empty glass can and stirred for 4 minutes at 2,000 rpm to form a dispersion. While stirring, 22.33 grams of a diisocyanate (available from Huntsman as Rubinate 1680) were injected into the resulting dispersion via a pre-weighed syringe. After the syringe was empty, the mixture resulting was stirred for a further 5 seconds, and 99.5 grams of this mixture were then poured into a plaque mold which had a volume of 311 centimeters$^3$ (21 centimeters Length×18.8 centimeters Width×1 centimeter Thickness). The mold temperature was at 50° C. to 55° C., and the curing time was 30 minutes resulting in a plaque density of about 0.315 gram/centimeters$^3$. Subsequently, the plaques were tested for mechanical properties after cutting into appropriate dog-bone shapes according to ASTM D3574. The mechanical properties are listed in Table 1. The bio-content of this plaque was 74.2 percent by weight.

The above foam is also tested for hydrolytic stability according to the following procedure. Plastic bottles (300 milliliters) are filled with distilled water (200 milliliters), and the above prepared dog-bone shaped foam material is hung using a string ensuring the foam material is completely immersed into the water. The product obtained is then placed in the oven and kept there for 2 weeks while maintaining the temperature in the range of 65° C. to 70° C. After the test period, a sample is removed from the water and dried in the oven at about 70° C. The ratio of mechanical properties after hydrolysis, divided by that before hydrolysis should be above about 80 percent for both tensile strength and percent elongation. For the polyurethane plaque of this Example, the stability is found to be 85 percent for tensile strength and 125 percent for elongation.

Example 13

Preparation of an insole plaque polyurethane foam derived from 56.8 weight percent (percent by weight) of polyol, 17.1 weight percent of the biobased diethyl succinate plasticizer, 21.1 weight percent of diisocyanate, 1.66 weight percent of chain extender, 2 weight percent of dye, 0.57 weight percent of catalyst, 0.31 weight percent of surfactant, 0.06 weight percent of crosslinker, and 0.5 weight percent of water.

56.8 Grams of the polyester resin of Example 6 were melted in a 400 milliliter glass can at 70° C. for 2 hours in an oven. To this was added 0.31 gram of TEGOSTAB® surfactant (available from Evonik), 1.6 grams of 1,3-propanediol (chain extender), 0.57 gram of DABCO LV® catalyst (available from Evonik), 0.5 gram of water, 0.06 gram of diethanol amine crosslinker, 2 grams of Red dye (available from BAO Shen Polyurethane Tech. LTD-China), 17.05 grams of biobased diethyl succinate, and the resulting mixture was stirred for 30 minutes at 2,000 rpm to ensure homogeneity. The mixture was then added to the empty glass can and stirred for 4 minutes at 2,000 rpm to form a dispersion. While stirring, 21.05 grams of a diisocyanate (available from Huntsman as Rubinate 1680) were injected into the resulting dispersion via a pre-weighed syringe. After the syringe was empty, the mixture resulting was stirred for a further 5 seconds, and 99.5 grams of this mixture were then poured into a plaque mold, which had a volume of 311 centimeters$^3$ (21 centimeters Length×18.8 centimeters Width×1 centimeters Thickness). The mold temperature was at 50° C. to 55° C., and the curing time was 30 minutes resulting in a plaque density of about 0.315 gram/centimeters$^3$. Subsequently, the plaques were tested for mechanical properties after cutting into appropriate dog-bone shapes according to ASTM D3574. The mechanical properties are listed in Table 1. The bio-content of this plaque was 75.5 percent by weight. For the polyurethane plaque of this Example, the hydrolytic stability using the procedure as described in Example 12 is found to be 83 percent for tensile strength and 120 percent for elongation.

TABLE 1

Mechanical Performance of the Polyurethane Plaques

| Examples | Density (g/cm$^3$) | Hardness (Asker C) | Rebound (%) | Die C Tear (N/mm) | Split Tear (N/mm) | Strength (ksc) | Elongation (%) |
|---|---|---|---|---|---|---|---|
| Example 12 | 0.315 | 36 | 42 | 7.0 | 1.4 | 13.1 | 346 |
| Example 13 | 0.315 | 32 | 53 | 5.6 | 1.32 | 10.5 | 335 |

Example 14

Preparation of an insole plaque polyurethane foam derived from 57.1 weight percent of polyol, 17.1 weight percent of the biobased dibutyl succinate plasticizer, 20.8 weight percent of diisocyanate, 1.67 weight percent of chain extender, 2 weight percent of dye, 0.29 weight percent of catalyst, 0.31 weight percent of surfactant, 0.06 weight percent of crosslinker, and 0.57 weight percent of water.

84 Grams of the polyester resin of Example 9 were melted in a 400 milliliter glass can at 70° C. for 2 hours in an oven. To this was added 0.462 gram of TEGOSTAB® surfactant (available from Evonik), 2.46 grams of 1,3-propanediol (chain extender), 0.42 gram of DABCO LV® catalyst (available from Evonik), 0.84 gram of water, 0.084 gram of diethanol amine crosslinker, 2.95 grams of Orange dye (available from BAO Shen Polyurethane Tech. LTD-China), 25.2 grams of biobased dibutyl succinate of Example 1, and the resulting mixture was stirred for 30 minutes at 2,000 rpm to ensure homogeneity. The mixture was then added to the empty glass can and stirred for 4 minutes at 2,000 rpm to form a dispersion. While stirring, 30.64 grams of a diisocyanate (available from Huntsman as Rubinate 1680) were injected into the resulting dispersion via a pre-weighed syringe. After the syringe was empty, the mixture resulting was stirred for a further 5 seconds, and 124.4 grams of this mixture were then poured into a plaque mold which had a volume of 311 centimeters$^3$ (21 centimeters Length×18.8 centimeters Width×1 centimeters Thickness). The mold temperature was at 50° C. to 55° C., and the curing time was 30 minutes resulting in a plaque density of about 0.4 gram/centimeters$^3$. Subsequently, the plaques were tested for mechanical properties after cutting into appropriate dog-bone shapes according to ASTM D3574. The mechanical properties are listed in Table 2. The bio-content of this plaque was 76 percent by weight. For the polyurethane plaque of this Example, the hydrolytic stability using the procedure as described in Example 12 is found to be 90 percent for tensile strength and 130 percent for elongation.

TABLE 2

Mechanical Performance of the Polyurethane Plaques

| Examples | Density (g/cm$^3$) | Hardness (Asker C) | Rebound (%) | Die C Tear (N/mm) | Split tear (N/mm) | Strength (ksc) | Elongation (%) |
|---|---|---|---|---|---|---|---|
| Example 14 | 0.4 | 34 | 35 | 4.2 | 1.1 | 0.76 | 194 |

Example 15

Preparation of a plaque polyurethane foam derived from 64.9 weight percent of polyol, 6.6 weight percent of the biobased bis(ethoxy-cardanolyl) sebacate plasticizer, 22.9 weight percent of diisocyanate, 1.9 weight percent of chain extender, 2.3 weight percent of dye, 0.65 weight percent of catalyst, 0.36 weight percent of surfactant, 0.07 weight percent of crosslinker, and 0.57 weight percent of water.

96 Grams of the polyester resin of Example 10 were melted in a 400 milliliter glass can at 70° C. for 2 hours in an oven. To this was added 0.528 gram of TEGOSTAB® surfactant (available from Evonik), 2.81 grams of 1,3-propanediol (chain extender), 0.96 gram of DABCO LV® catalyst (available from Evonik), 0.845 gram of water, 0.096 gram of diethanol amine crosslinker, 3.37 grams of Orange dye (available from BAO Shen Polyurethane Tech. LTD-China), 9.66 grams of biobased bis(ethoxy-cardanolyl) sebacate of Example 5, and the resulting mixture was stirred for 30 minutes at 2,000 rpm to ensure homogeneity. The mixture was then added to the empty glass can and stirred for 4 minutes at 2,000 rpm to form a dispersion. While stirring, 33.69 grams of a diisocyanate (available from Huntsman as Rubinate 1680) were injected into the resulting dispersion via a pre-weighed syringe. After the syringe was empty, the mixture resulting was stirred for a further 5 seconds, and 124.4 grams of this mixture are then poured into a plaque mold which had a volume of 311 centimeters$^3$ (21 centimeters Length×18.8 centimeters Width×1 centimeters Thickness). The mold temperature was at 50° C. to 55° C., and the curing time was 30 minutes resulting in a plaque density of about 0.4 gram/centimeters$^3$. Subsequently, the plaques were tested for mechanical properties after cutting into appropriate dog-bone shapes according to ASTM D3574. The mechanical properties are listed in Table 3. The bio-content of this plaque was 73.4 percent by weight. For the polyurethane plaque of this Example, the hydrolytic stability using the procedure as described in Example 12, is found to be 90 percent for tensile strength and 125 percent for elongation.

Example 16

Preparation of a plaque polyurethane foam derived from 63.75 weight percent of polyol, 6.38 weight percent of the biobased bis(ethoxy-cardanolyl) sebacate plasticizer, 24.1 weight percent of diisocyanate, 1.87 weight percent of chain extender, 2.24 weight percent of dye, 0.56 weight percent of catalyst, 0.35 weight percent of surfactant, 0.06 weight percent of crosslinker, and 0.56 weight percent of water.

94 Grams of the polyester resin of Example 11 were melted in a 400 milliliter glass can at 70° C. for 2 hours in an oven. To this was added 0.517 gram of TEGOSTAB® surfactant (available from Evonik), 2.75 grams of 1,3-propanediol (chain extender), 0.94 gram of DABCO LV® catalyst (available from Evonik), 0.827 gram of water, 0.094 gram of diethanol amine crosslinker, 3.3 grams of Orange dye (available from BAO Shen Polyurethane Tech. LTD-China), 9.4 grams of biobased bis(ethoxy-cardanolyl) sebacate of Example 5, and the resulting mixture was stirred for 30 minutes at 2,000 rpm to ensure homogeneity. The mixture was then added to the empty glass can and stirred for 4 minutes at 2,000 rpm to form a dispersion. While stirring, 35.6 grams of a diisocyanate (available from Huntsman as Rubinate 1680) were injected into the resulting dispersion via a pre-weighed syringe. After the syringe was empty, the mixture resulting was stirred for a further 5 seconds, and 124.4 grams of this mixture were then poured into a plaque mold which had a volume of 311 centimeters$^3$ (21 centimeters Length×18.8 centimeters Width×1 centimeters Thickness). The mold temperature was at 50° C. to 55° C., and the curing time was 30 minutes resulting in a plaque density of about 0.4 gram/centimeters$^3$. Subsequently, the plaques were tested for mechanical properties after cutting into appropriate dog-bone shapes according to ASTM D3574. The mechanical properties are listed in Table 3. The bio-content of this plaque was 72.1 percent by weight. For the polyurethane plaque of this Example, the hydrolytic stability using the procedure as described in Example 12 is found to be 95 percent for tensile strength and 125 percent for elongation.

Example 17

Preparation of a plaque polyurethane foam derived from 62.9 weight percent of polyol, 6.29 weight percent of the biobased bis(ethoxy-cardanolyl) sebacate plasticizer, 25.1 weight percent of diisocyanate, 1.85 weight percent of chain extender, 2.21 weight percent of dye, 0.63 weight percent of catalyst, 0.35 weight percent of surfactant, 0.06 weight percent of crosslinker, and 0.55 weight percent of water.

94 Grams of the polyester resin of Example 9 were melted in a 400 milliliter glass can at 70° C. for 2 hours in an oven. To this was added 0.484 gram of TEGOSTAB® surfactant (available from Evonik), 2.58 grams of 1,3-propanediol (chain extender), 0.88 gram of DABCO LV® catalyst (available from Evonik), 0.774 gram of water, 0.088 gram of diethanol amine crosslinker, 3.09 grams of Orange dye (available from BAO Shen Polyurethane Tech. LTD-China), 8.8 grams of biobased bis(ethoxy-cardanolyl) sebacate of Example 5, and the resulting mixture was stirred for 30 minutes at 2,000 rpm to ensure homogeneity. The mixture was then added to the empty glass can and stirred for 4 minutes at 2,000 rpm to form a dispersion. While stirring, 35.1 grams of a diisocyanate (available from Huntsman as Rubinate 1680) were injected into the resulting dispersion via a pre-weighed syringe. After the syringe was empty, the mixture resulting was stirred for a further 5 seconds and 124.4 grams of this mixture were then poured into a plaque mold which had a volume of 311 centimeters$^3$ (21 centimeters Length×18.8 centimeters Width×1 centimeters Thickness). The mold temperature was at 50° C. to 55° C., and the curing time was 30 minutes resulting in a plaque density of about 0.4 gram/centimeters$^3$. Subsequently, the plaques were tested for mechanical properties after cutting into appropriate dog-bone shapes according to ASTM D3574. The mechanical properties are listed in Table 3. The biocontent of this plaque was 71.1 percent by weight. For the polyurethane plaque of this Example, the hydrolytic stability using the procedure as described in Example 12 was found to be 90 percent for tensile strength and 120 percent for elongation.

TABLE 3

Mechanical Performance of the Polyurethane Plaques

| Examples | Density (g/cm3) | Hardness (Asker C) | Rebound (%) | Die C Tear (N/mm) | Split tear (N/mm) | Strength (ksc) | Elongation (%) |
|---|---|---|---|---|---|---|---|
| Example 15 | 0.4 | 30-35 | 30-35 | 4.0-4.5 | 1.5-2.0 | 2.5-3.0 | 200-250 |
| Example 16 | 0.4 | 35-40 | 35-40 | 4.5-5.0 | 1.5-2.0 | 3.0-3.5 | 250-300 |
| Example 17 | 0.4 | 35-40 | 40-45 | 6.0-v7.0 | 2.0-2.5 | 3.0-3.5 | 300-350 |
| Example 18 | 0.4 | 35-40 | 35-40 | 5.5-6.0 | 2.0-2.5 | 3.0-3.5 | 25-300 |

Specific embodiments of the present disclosure as illustrated in the following Examples are for illustrative purposes and are not limited to the materials, conditions, or process parameters set forth in these embodiments. Percent by weight is a known quantity and is usually based on the total of the components present. Molecular weights were provided by the sources involved, or by GPC, and from about to about includes all the values in between and some values that exceed or may not exceed the values disclosed. Also, the components of (a) to (h) can be mixed in various sequences to obtain the polyurethane elastomers and the polyurethane foams, both of which can be biodegradable. The viscosities were measured by the Brookfield CAP2000 Viscometer.

What is claimed is:

1. A polyurethane elastomer derived from:
   a plasticizer comprising a biobased bis(ethyl) succinate;
   a biobased polyester resin comprising terpoly(1,2-propylene succinate)-terpoly(1,3-propylene succinate)-terpoly(12-hydroxy stearate); and
   a) an organic diisocyanate, (b) a chain extender, (c) a crosslinker, (d) a surfactant, (e) an optional foaming agent, (f) an optional colorant, and (g) a catalyst.

2. The polyurethane elastomer of claim 1 wherein the foaming agent is present, said colorant is present and is comprised of a dye or a pigment, and wherein said organic diisocyanate is selected from the group consisting of diphenylmethane 4,4'-diisocyanate, isophorone diisocyanate, dicyclohexylmethane 4,4-diisocyanate, hexamethylene 1,6-diisocyanate, naphthalene 1,5-diisocyanate, and mixtures thereof.

3. The polyurethane elastomer of claim 1 wherein said biobased polyester resin further comprises poly(1,2-propylene-succinate), poly(1,2-propylene-sebacate), poly(1,3-propylene-succinate), poly(1,3-propylene-sebacate), poly(1,4-butylene-succinate), poly(1,4-butylene-sebacate), poly(1,2-propylene-azeleate), copoly(1,2-propylene succinate)-copoly(1,3-propylene succinate), copoly(1,2-propylene sebacate)-copoly(1,3-propylene sebacate), poly-12-hydroxy stearate, poly-ricinoleate, copoly(1,2-propylene succinate)-copoly(12-hydroxy stearate), copoly(1,2-propylene-sebacate)-copoly(12-hydroxy stearate), copoly(1,3-propylene succinate)-copoly(12-hydroxy stearate), copoly(1,3-propylene sebacate)-copoly(12-hydroxy stearate), copoly(1,2-propylene succinate)-copoly(1,2-propylene sebacate), copoly(1,3-propylene succinate)-copoly(1,3-propylene sebacate), copoly(1,2-propylene succinate)-copoly(ricinoleate), copoly(1,2-propylene-sebacate)-copoly-(ricinoleate), copoly(1,3-propylene succinate)-copoly(ricinoleate), copoly(1,3-propylene sebacate) copoly(12-ricinoleate), or terpoly(1,2-propylene succinate)-terpoly(1,3-propylene-succinate)-terpoly(ricinoleate).

4. The polyurethane elastomer of claim 1 wherein the hydrolytic stability is from about 80 to about 100 percent for tensile strength, and from about 100 to about 150 percent for elongation.

5. The polyurethane elastomer of claim 1 wherein said plasticizer further comprises a biobased di-methyl succinate, biobased bis(n-butyl) succinate, biobased bis(propyl) succinate, biobased bis(2-butyl) succinate, biobased bis(2-octyl) succinate, biobased bis(12-alkyl stearyl) succinate, biobased dimethyl sebacate, biobased diethyl sebacate or biobased bis(ethyl) sebacate, biobased bis(n-butyl) sebacate, biobased bis(propyl) sebacate, biobased bis(2-butyl) sebacate, biobased bis(2-octyl) sebacate, biobased bis(12-alkyl stearylol) succinate, biobased bis(12-alkyl stearylol) sebacate, biobased bis(12-alkyl ricinoloyl) succinate, and biobased bis(12-alkyl ricinoloyl) sebacate, or mixtures thereof.

\* \* \* \* \*